(12) United States Patent
Park et al.

(10) Patent No.: US 10,199,282 B2
(45) Date of Patent: Feb. 5, 2019

(54) INSPECTION APPARATUS AND METHOD OF MANUFACTURING SEMICONDUCTOR DEVICE USING THE SAME

(71) Applicant: Samsung Electronics Co., Ltd., Suwon-si, Gyeonggi-do (KR)

(72) Inventors: Sung-Won Park, Yongin-si (KR); Jeong-Su Ha, Suwon-si (KR); Sangbong Park, Yongin-si (KR); Kwang Soo Kim, Pyeongtaek-si (KR); Byeong Kyu Cha, Seoul (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 0 days.

(21) Appl. No.: 15/626,302

(22) Filed: Jun. 19, 2017

(65) Prior Publication Data

US 2018/0144998 A1    May 24, 2018

(30) Foreign Application Priority Data

Nov. 23, 2016    (KR) .................. 10-2016-0156716

(51) Int. Cl.
   *H01L 21/66*    (2006.01)
   *G01N 21/95*    (2006.01)
   *G01N 21/88*    (2006.01)
   *G06T 7/00*     (2017.01)
   *H04N 7/18*     (2006.01)

(52) U.S. Cl.
   CPC .......... *H01L 22/20* (2013.01); *G01N 21/8806* (2013.01); *G01N 21/8851* (2013.01); *G01N 21/9501* (2013.01); *G06T 7/0004* (2013.01); *H01L 22/12* (2013.01); *H04N 7/181* (2013.01); *G01N 2021/8887* (2013.01); *G06T 2207/10056* (2013.01); *G06T 2207/30148* (2013.01)

(58) Field of Classification Search
   CPC ......... H01L 22/12; H01L 22/20; H01L 22/24; G01N 21/8806; G01N 21/8851; G01N 21/9501; G01N 2021/8887; G06T 7/0004; G06T 2207/10056; G06T 2207/30148
   See application file for complete search history.

(56) References Cited

U.S. PATENT DOCUMENTS

| | | | |
|---|---|---|---|
| 7,002,676 B2 | 2/2006 | Akiyama | |
| 7,463,350 B2 | 12/2008 | Nishiyama et al. | |
| 7,528,943 B2 | 5/2009 | Brown et al. | |
| 8,467,048 B2 | 6/2013 | Nishiyama et al. | |
| 8,482,727 B2 | 7/2013 | Nakao et al. | |
| 8,624,971 B2 | 1/2014 | Brown et al. | |
| 2002/0054703 A1* | 5/2002 | Hiroi | G01N 21/9501 382/149 |

(Continued)

FOREIGN PATENT DOCUMENTS

KR    20110066778 A    6/2011

*Primary Examiner* — Stephen W Smoot
(74) *Attorney, Agent, or Firm* — Harness, Dickey & Pierce, P.L.C.

(57) ABSTRACT

Disclosed are an inspection apparatus and a method of manufacturing a semiconductor device using the same. The inspection apparatus includes a stage configured to receive a substrate, an objective lens on the stage and configured to enlarge the substrate optically, an ocular lens on the objective lens and configured to form at its image plane an image of the substrate, and a plurality of sensors above the ocular lens and in the image plane of the ocular lens.

20 Claims, 9 Drawing Sheets

(56) References Cited

U.S. PATENT DOCUMENTS

| | | | |
|---|---|---|---|
| 2004/0086171 A1* | 5/2004 | Jun ................... | G01N 21/9503 |
| | | | 382/149 |
| 2009/0213215 A1* | 8/2009 | Shibata .............. | G01N 21/9501 |
| | | | 348/92 |
| 2015/0116717 A1* | 4/2015 | Manassen .............. | G01N 21/55 |
| | | | 356/445 |
| 2016/0018328 A1* | 1/2016 | Kim ................... | G01N 21/9501 |
| | | | 356/237.5 |
| 2016/0125590 A1* | 5/2016 | Yoshida ............. | G01N 21/9501 |
| | | | 348/87 |

* cited by examiner

INSPECTION APPARATUS AND METHOD OF MANUFACTURING SEMICONDUCTOR DEVICE USING THE SAME

CROSS-REFERENCE TO RELATED APPLICATIONS

This U.S. nonprovisional patent application claims priority under 35 U.S.C. § 119 to Korean Patent Application No. 10-2016-0156716, filed on Nov. 23, 2016, the entire contents of which are hereby incorporated by reference.

BACKGROUND

Inventive concepts relate to an inspection apparatus, and more particularly, to an inspection apparatus and/or a method of manufacturing a semiconductor device using the same that inspects defects of the semiconductor device.

With the advancement of high integration of semiconductor devices, fabrication processes are becoming variously complicated. In addition, a substrate inspection process may be performed after each process is done. For example, an inspection apparatus may optically detect defects on a substrate. The defects may include pattern defects and/or particle defects.

SUMMARY

Inventive concepts relate to an inspection apparatus and/or a method of manufacturing a semiconductor device using the same capable of increasing image processing speeds.

Some example embodiments of inventive concepts provide an inspection apparatus and a method of manufacturing a semiconductor device using the same capable of increasing quantity of reflected light.

According to some example embodiments of inventive concepts, an inspection apparatus may include a stage configured to receive a substrate, an objective lens on the stage and configured to enlarge the substrate optically, an ocular lens on the objective lens and configured to form at its image plane an image of the enlarged substrate, and a plurality of sensors above the ocular lens and in the image plane of the ocular lens.

According to some example embodiments of inventive concepts, a method of manufacturing a semiconductor device may include performing a first manufacturing process on a substrate, inspecting the substrate using an inspection apparatus to detect a level of defects on the substrate, and performing a second manufacturing process on the substrate based on the level of defects on the substrate detected during the inspecting the substrate. The inspection apparatus may include a stage configured to receive a substrate, an objective lens on the stage and configured to enlarge the substrate optically, an ocular lens on the objective lens and configured to form at its image plane an image of the enlarged substrate, and a plurality of sensors above the ocular lens and in the image plane of the ocular lens.

According to some example embodiments of inventive concepts, an inspection apparatus may include a stage configured to receive a substrate and to move the substrate in a first direction, an optical system configured to form an enlarged image of the substrate at an image plane, and a plurality of sensors arranged in the image plane. The plurality of sensors are configured to sense part of the enlarged image of the substrate. The plurality of sensors include a first sensor and a second sensor. The first sensor includes an overlapping region that is spaced apart from an overlapping region of the second sensor in the first direction.

DETAILED DESCRIPTION

Figure 1:
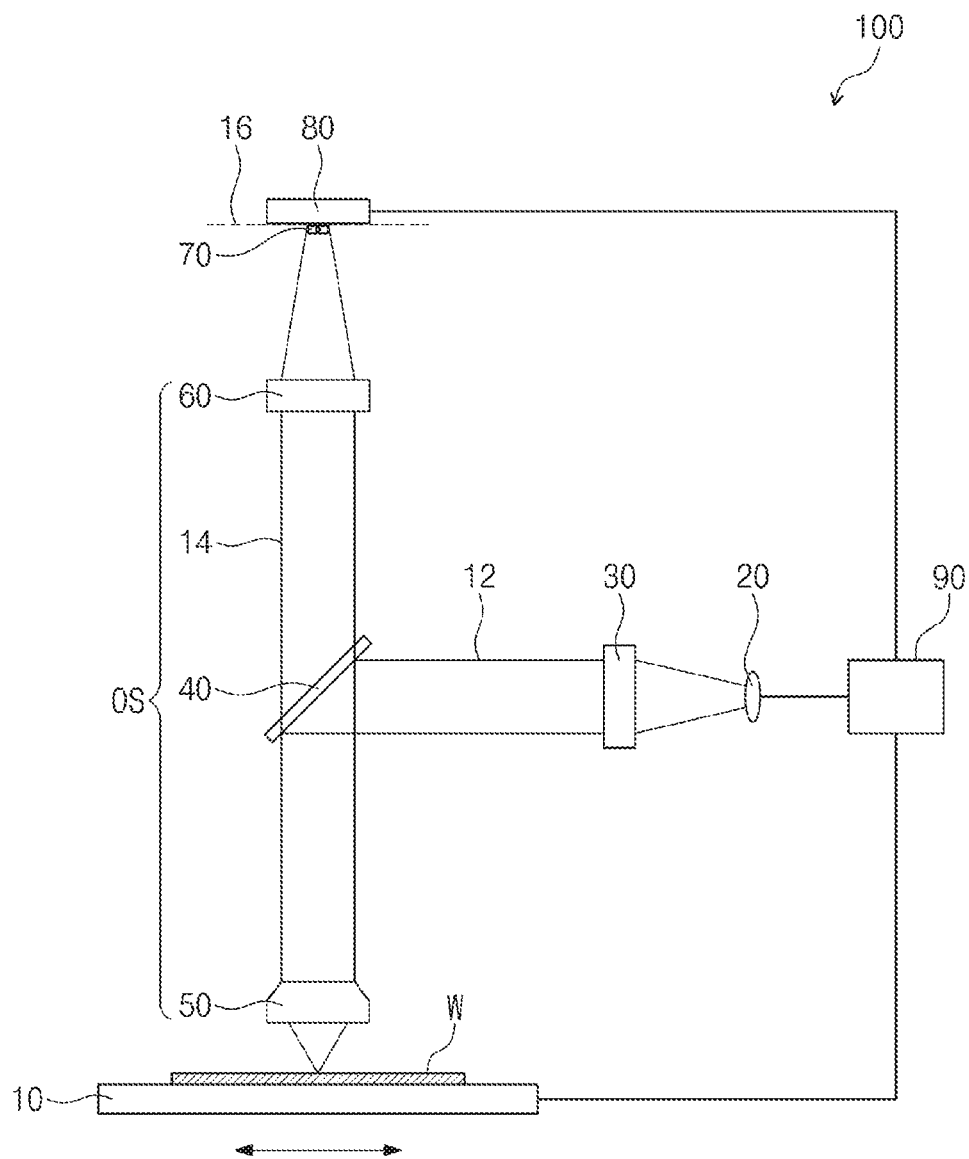
FIG. 1 is a schematic diagram illustrating an inspection apparatus according to some example embodiments of inventive concepts.

FIG. 1 is a schematic diagram illustrating an inspection apparatus 100 according to some example embodiments of inventive concepts.

Referring to FIG. 1, the inspection apparatus 100 may include an optical microscope. Alternatively, the inspection apparatus 100 include be an electron microscope. In some example embodiments, the inspection apparatus 100 may include a stage 10, a light source 20, a collimator 30, an optical system OS, sensors 70, a printed circuit board 80, and a control module 90. The optical system OS may include an objective lens 50, a beam splitter 40, and an ocular lens 60.

The stage 10 may be configured to receive a substrate W. For example, the substrate W may include a silicon wafer. Alternatively, the substrate W may include a glass substrate or a compound semiconductor substrate. The stage 10 may move the substrate W relative to the objective lens 50.

Figure 2:
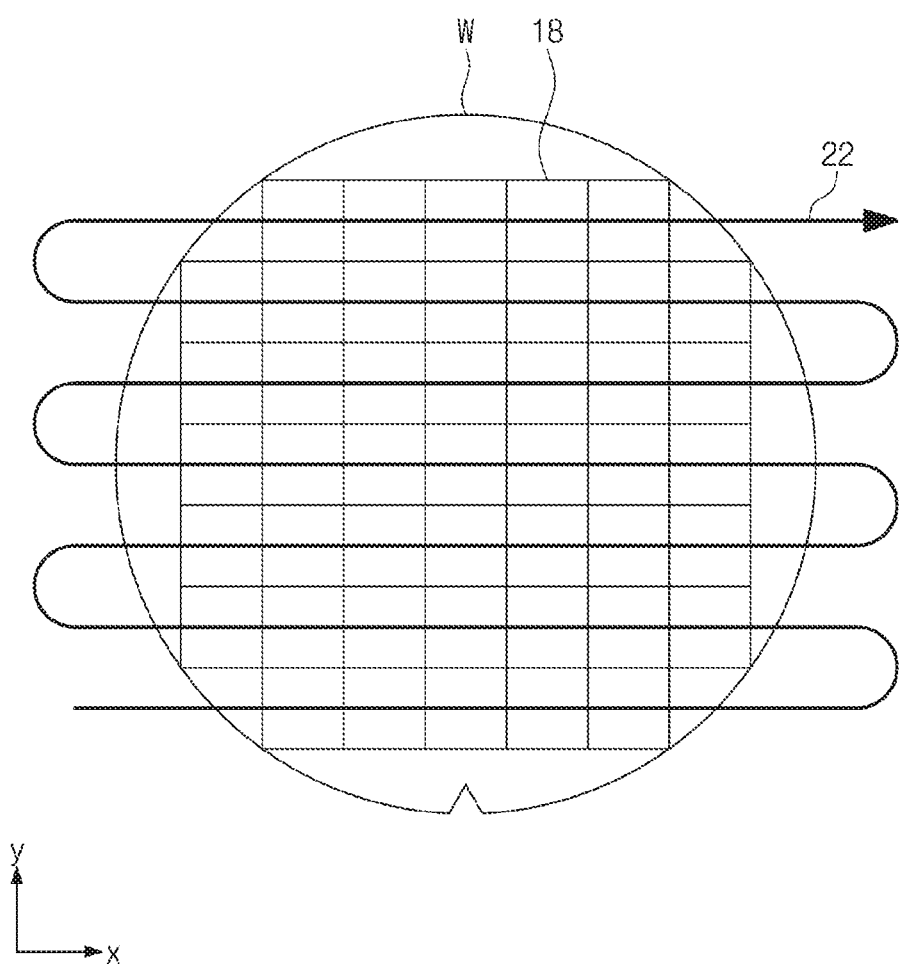
FIG. 2 is a plan view illustrating a substrate of FIG. 1.

FIG. 2 shows the substrate W of FIG. 1.

Referring to FIGS. 1 and 2, the substrate W may be scanned by movement of the stage 10. For example, the stage 10 may move the substrate W in a reverse direction to a scan direction 22 relative to the objective lens 50, the ocular lens 60, and the sensors 70. The sensors 70 may detect a front side image of the substrate W along a movement path of the stage 10. For example, when the scan direction 22 is an x-direction, the stage 10 may move the substrate W in a reverse direction to the x-direction. Alternatively, the stage 10 may move the substrate W in the x-direction. Inventive concepts are not limited thereto, however. For example, in some example embodiments, the stage 10 may move the substrate W in the x-, y-, and/or z-directions.

The substrate W may include a plurality of semiconductor devices 18. As one example, each of the semiconductor devices 18 may include an image sensor. As another example, the semiconductor devices 18 may include a memory device or an AP (Application Processor). As other example, the semiconductor devices 18 may include a display device or an LED (Light Emitting Diode). The substrate W may have a diameter of, for example, about 6 inches, but is not limited thereto.

Referring back to FIG. 1, the light source 20 may generate an incident light 12. For example, the light source 20 may include an illumination system having a mercury lamp, a laser diode, or an LED (Light Emitting Diode). The incident light 12 may include visible light. Alternatively, the incident light 12 may include ultraviolet or infrared light.

The collimator 30 may be installed between the light source 20 and the beam splitter 40. The collimator 30 may cause the incident light 12 to become a parallel beam.

The beam splitter 40 may be installed between the objective lens 50 and the ocular lens 60. The beam splitter 40 may reflect at least a portion (e.g., some or all) of the incident light 12 to the objective lens 50. The beam splitter 40 may allow a reflected light 14 to pass therethrough.

The objective lens 50 may be disposed adjacent to the substrate W and the stage 10. In some example embodiments, the objective lens 50 may enlarge the substrate W optically. In other words, the objective lens 50 may magnify an image (or view) of the substrate W. The objective lens 50 may have resolution determined by its numerical aperture (NA). The objective lens 50 may focus the incident light 12 on the substrate W. The incident light 12 may be reflected from the substrate W to produce the reflected light 14. The reflected light 14 may be provided to the objective lens 50. The reflected light 14 may be provided from the objective lens 50 to the beam splitter 40. The ocular lens 60 may receive the reflected light 14 passing through the beam splitter 40.

The ocular lens 60 may provide the reflected light 14 to the sensors 70. For example, the ocular lens 60 may focus the reflected light 14 on the sensors 70. In some example embodiments, the substrate W may be imaged on the sensors 70 by the objective lens 50. The inspection apparatus 100 may have enlargement magnification of an image of the substrate W that is determined by the product of magnifications of the objective lens 50 and the ocular lens 60.

The sensors 70 may be installed above the ocular lens 60. In some example embodiments, the sensors 70 may be disposed between the ocular lens 60 and the printed circuit board 80. For example, each of the sensors 70 may include a CCD (Charged Coupled Device) or CMOS sensor.

Figure 3:
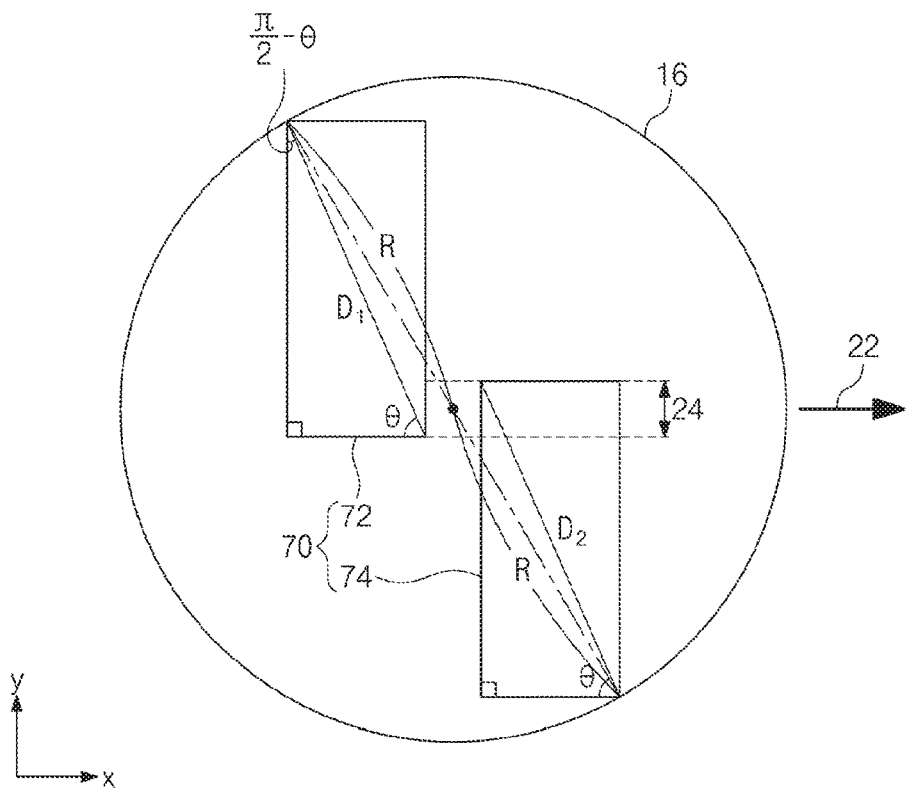
FIG. 3 is a plan view illustrating sensors of FIG. 1.

FIG. 3 shows the sensors 70 of FIG. 1.

Referring to FIG. 3, the sensors 70 may be disposed in an image plane 16 of the ocular lens 60. In some example embodiments, the sensors 70 may include a first sensor 72 and a second sensor 74. The first and second sensors 72 and 74 may be TDI (Time Delay and Integration) sensors and/or TDI line scan sensors. For example, the image plane 16 may have a circular shape and the sensors 70 may have a shape corresponding to a quadrangle in the circular shape of the image plane 16. Each of the first and second sensors 72 and 74 may partially detect an image of the substrate W in the image plane 16. The first and second sensors 72 and 74 may have a quadrangular shape. The first and second sensors 72 and 74 may have corners (e.g., vertices) lying on a perimeter of the image plane 16. The first and second sensors 72 and 74 may have the same numbers of pixels.

The first sensor 72 may have a rectangular shape. The first sensor 72 may have a first diagonal D1 greater than a radius R of the image plane 16.

The second sensor 74 may have a shape the same as that of the first sensor 72. For example, the second sensor 74 may have a rectangular shape. The second sensor 74 may have the same size as that of the first sensor 72. The second sensor 74 may have the same resolution as that of the first sensor 72. The second sensor 74 may have a second diagonal D2 greater than the radius R of the image plane 16.

In some example embodiments, the first and second sensors 72 and 74 may be arranged in the image plane 16 along a y-direction. The first and second sensors 72 and 74 may have overlapping regions 24. The overlapping region 24 may have a width that is defined by a length in a direction vertical to the scan direction 22. For example, the scan direction 22 may be the same as those of horizontal lengths of the first and second sensors 72 and 74. The scan direction 22 and the horizontal length directions of the first and second sensors 72 and 74 may be the x-direction. The scan direction 22 may be perpendicular to directions of vertical lengths of the first and second sensors 72 and 74. The vertical lengths of the first and second sensors 72 and 74 may be y-directional lengths. For example, each of the first and second sensors 72 and 74 may have the horizontal and/or vertical lengths in the range from about 10 μm to about 2 cm. For example, as shown in FIG. 3, the overlapping region 24 of the first sensor 72 may be spaced apart from the overlapping region 24 of the second sensor 74 in the scan direction 22.

Figure 4:
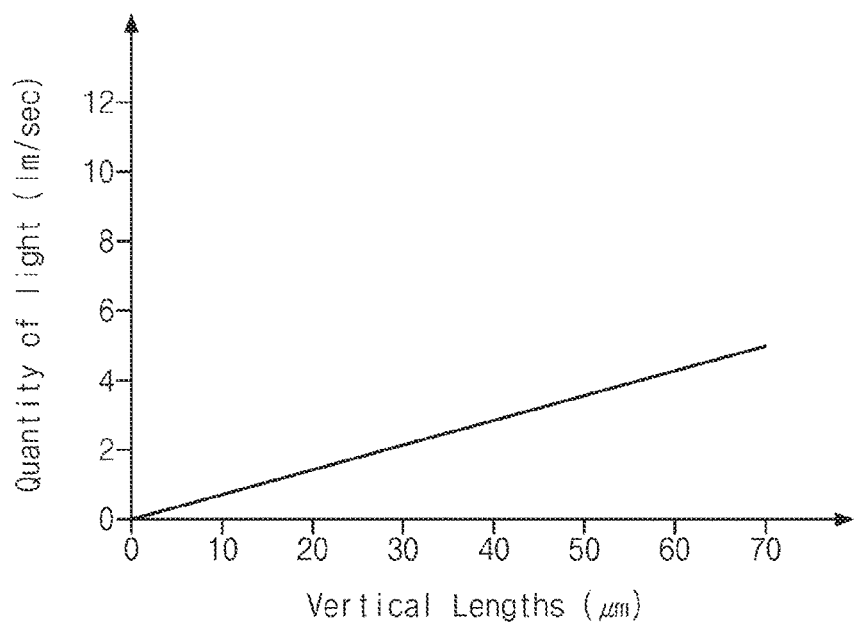
FIG. 4 is a graph illustrating quantity of light versus vertical lengths of first and second sensors shown in FIG. 3.

FIG. 4 shows how quantity of light changes with the vertical lengths of the first and second sensors 72 and 74 of FIG. 3.

Referring to FIGS. 1, 3, and 4, the quantity of light may be in proportion to the vertical lengths (e.g., y-directional lengths) of the first and second sensors 72 and 74. The quantity of light may be defined by quantity of the reflected light 14 detected by the first and second sensors 72 and 74. For example, the quantity of light may increase with increasing the vertical lengths of the first and second sensors 72 and 74. An increase in quantity of the reflected light 14 may reduce distortion of detected images of the first and second sensors 72 and 74. The quantity of light may determine brightness, color tone, and/or luminous intensity of an image.

Figure 5:
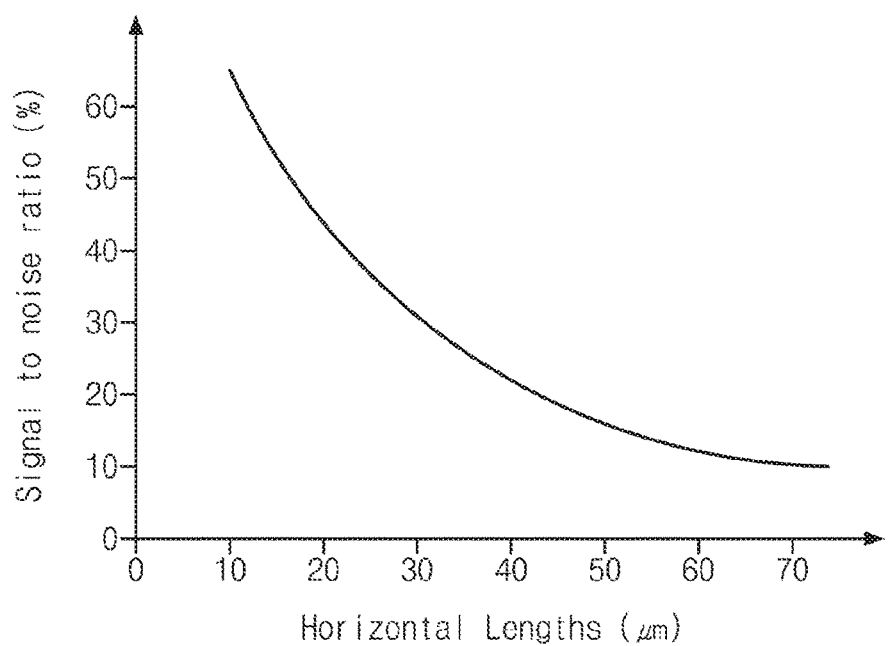
FIG. 5 is a graph illustrating signal-to-noise ratio versus horizontal lengths of first and second sensors shown in FIG. 3.

FIG. 5 shows how signal-to-noise ratio changes with horizontal lengths of the first and second sensors 72 and 74 of FIG. 3.

Referring to FIG. 5, the signal-to-noise ratio may be in inverse proportion to the horizontal lengths (e.g., x-directional lengths) of the first and second sensors 72 and 74. For example, the signal-to-noise ratio may decrease with increasing the horizontal lengths of the first and second sensors 72 and 74.

Referring to FIGS. 3 to 5, the horizontal and vertical lengths of the first and second sensors 72 and 74 may be calculated from a tilt angle θ and the first and second diagonals D1 and D2. In some example embodiments, the tilt angle θ may be an angle between the first diagonal D1 and a horizontal side of the first sensor 72 adjacent to a center of the image plane 16. Alternatively, the tilt angle θ may be an angle between the second diagonal D2 and a horizontal side of the second sensor 74 far away from the center of the image plane 16. When the first and second diagonals D1 and D2 are the same as the radius R of the image plane 16, the horizontal and/or vertical lengths of each of the first and second sensors 72 and 74 may be calculated based on the tilt angle θ. For example, the radius R of the image plane 16 may be equal to or less than about 1 cm.

The tilt angle θ may increase with increasing the vertical length. For example, the vertical length may be proportional to a sine function of the tilt angle θ. The vertical length may correspond to the product of sin θ and one of the first and second diagonals D1 and D2.

The tilt angle θ may decrease with increasing the horizontal length. For example, the horizontal length may be proportional to a cosine function of the tilt angle θ. The horizontal length may correspond to the product of cos θ and one of the first and second diagonals D1 and D2. Accordingly, the quantity of light and the signal-to-noise ratio may be expressed by the tilt angle θ.

Figure 6:
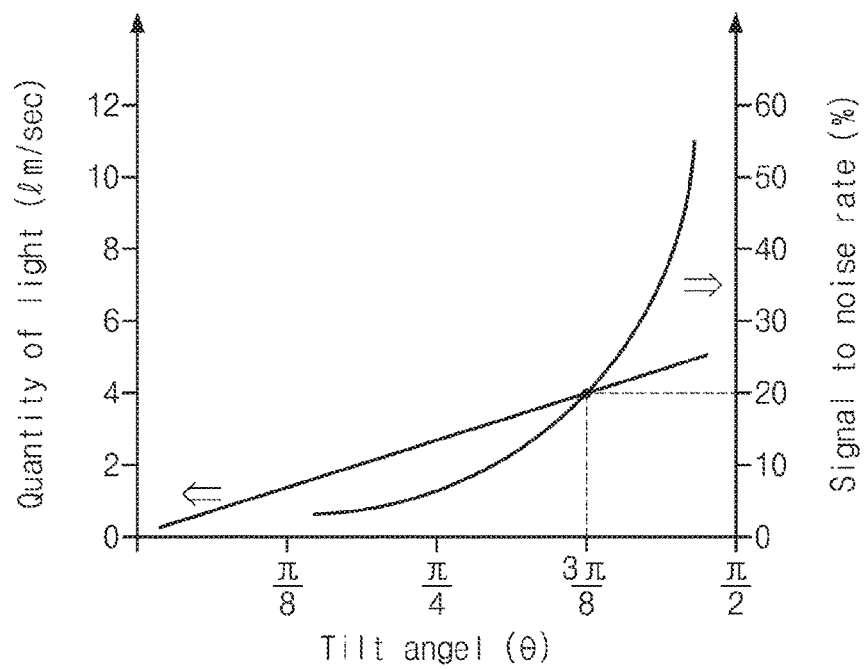
FIG. 6 is a graph illustrating quantity of light and signal-to-noise ratio each versus tilt angle shown in FIG. 3.

FIG. 6 shows how quality of light and signal-to-noise ratio change with the tilt angle θ of FIG. 3.

Referring to FIG. 6, the quantity of light and the signal-to-noise ratio may increase with increasing the tilt angle θ. For example, when the tilt angle θ is 3π/8, a curve representing the quantity of light may cross a curve representing the signal-to-noise. The quantity of light may be approximately 4 lm/sec when the tilt angle θ is 3π/8. The signal-to-noise ratio may be approximately 20% when the tilt angle θ is 3π/8. When the tilt angle θ increases from 3π/8 to π/2, the signal-to-noise ratio may remarkably increase from 20% to 100%. When the signal-to-noise ratio is above 20%, defects may be hardly detected due to noise. When the tilt angle θ decreases below 3π/8, the quantity of light may be reduced to bring about image distortion of the substrate W.

Figure 7:
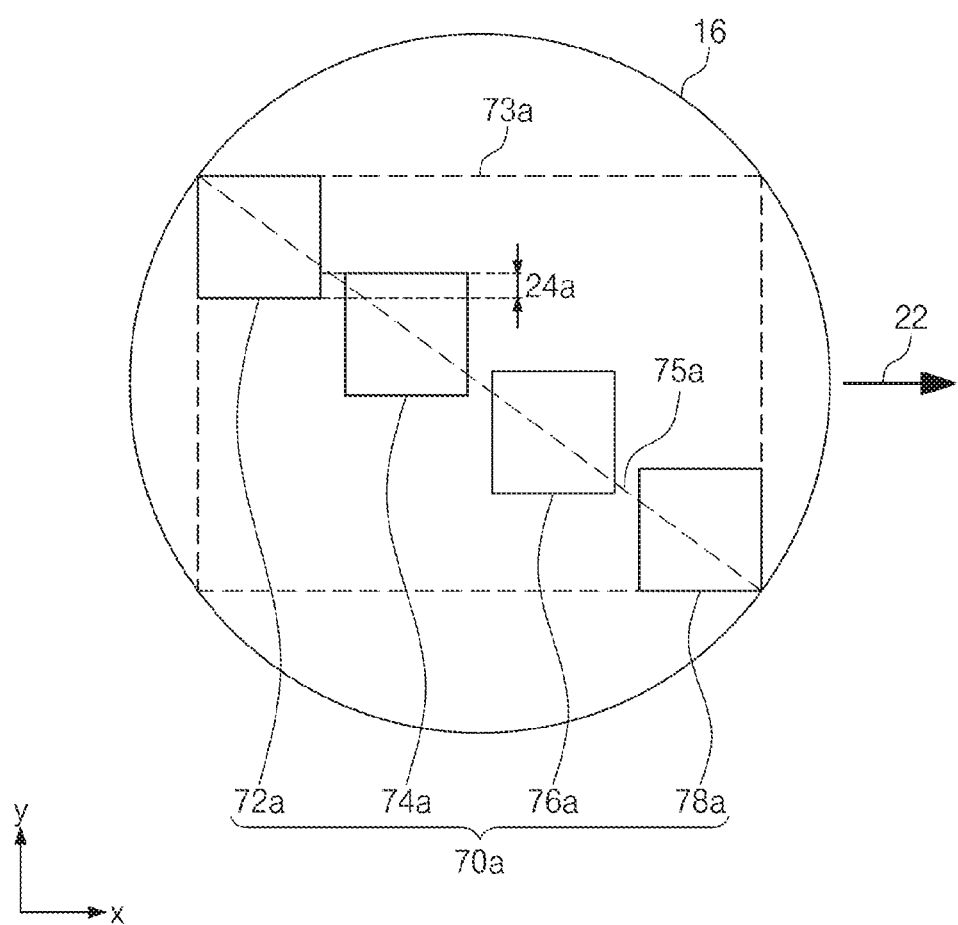
FIG. 7 is a plan view illustrating an example of sensors shown in FIG. 1.

FIG. 7 is a plan view illustrating an example of sensors shown in FIG. 1.

Referring to FIG. 7, the inspection apparatus 100 of FIG. 1 may be equipped with sensors 70a, which include first, second, third, and fourth sensors 72a, 74a, 76a, and 78a. The first to fourth sensors 72a to 78a may have the same size, shape, and resolution. For example, each of the first to fourth sensors 72a to 78a may have a quadrangular shape. Each of the first to fourth sensors 72a to 78a may partially detect an image of the substrate W in the image plane 16. The first to fourth sensors 72a to 78a may have overlapping regions 24a. The first to fourth sensors 72a to 78a may be arranged in a diameter direction of the image plane 16. In some example embodiments, the first to fourth sensors 72a to 78a may be arranged in a direction of a diagonal 75a of a phantom rectangle 73a having vertices on the perimeter of the image plane 16. The direction of the diagonal 75a may be defined by a direction between the x-direction and the y-direction. The first to fourth sensors 72a to 78a arranged in the direction of the diagonal 75a may take the place of a large-sized sensor (not shown) whose size corresponds to the phantom rectangle 73a.

Figure 8:
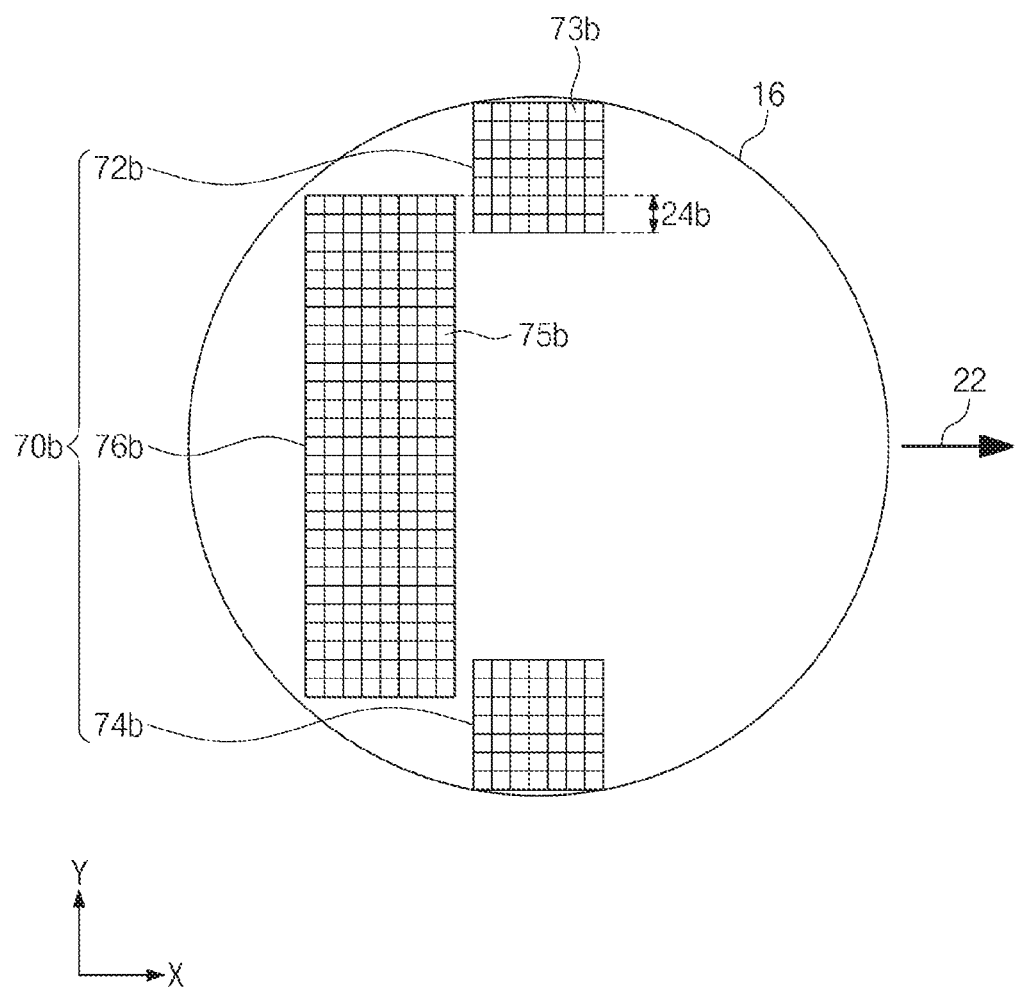
FIG. 8 is a plan view illustrating an example of sensors shown in FIG. 1.

FIG. 8 is a plan view illustrating an example of sensors shown in FIG. 1.

Referring to FIG. 8, the inspection apparatus 100 of FIG. 1 may be equipped with sensors 70b, which include a first edge sensor 72b, a second edge sensor 74b, and a central sensor 76b. The first and second edge sensors 72b and 74b and the central sensor 76b may have overlapping regions 24b that overlap in the scan direction 22.

The first and second edge sensors 72b and 74b may be disposed adjacent to the perimeter of the image plane 16. Each of the first and second edge sensors 72b and 74b may be smaller than the central sensor 76b. The first edge sensor 72b may be disposed above the central sensor 76b in the y-direction. The second edge sensor 74b may be disposed below the central sensor 76b in the y-direction. In some example embodiments, each of the first and second edge sensors 72b and 74b may have first pixels 73b.

Referring to FIGS. 4 and 8, the first and second edge sensors 72b and 74b may serve as vertically extended portions of the central sensor 76b. It may thus be possible to increase and/or maximize quantity of light incident onto the sensors 70b.

Referring to FIG. 8, the image plane 16 may include the central sensor 76b adjacent to its center between the first and second edge sensors 72b and 74b. The central sensor 76b may be interposed between the first and second edge sensors 72b and 74b. In some example embodiments, the central sensor 76b may have second pixels 75b. For example, the second pixels 75b may have a size the same as that of the first pixels 73b. Accordingly, each of the first and second edge sensors 72b and 74b may have the same resolution as that of the central sensor 76b.

Referring back to FIG. 1, the printed circuit board 80 may be mounted with the sensors 70. The printed circuit board 80 may have a top surface corresponding to the image plane 16. Alternatively, the printed circuit board 80 may be mounted with the control module 90.

The control module 90 may control the stage 10, the light source 20, and the sensors 70.

Figure 9:
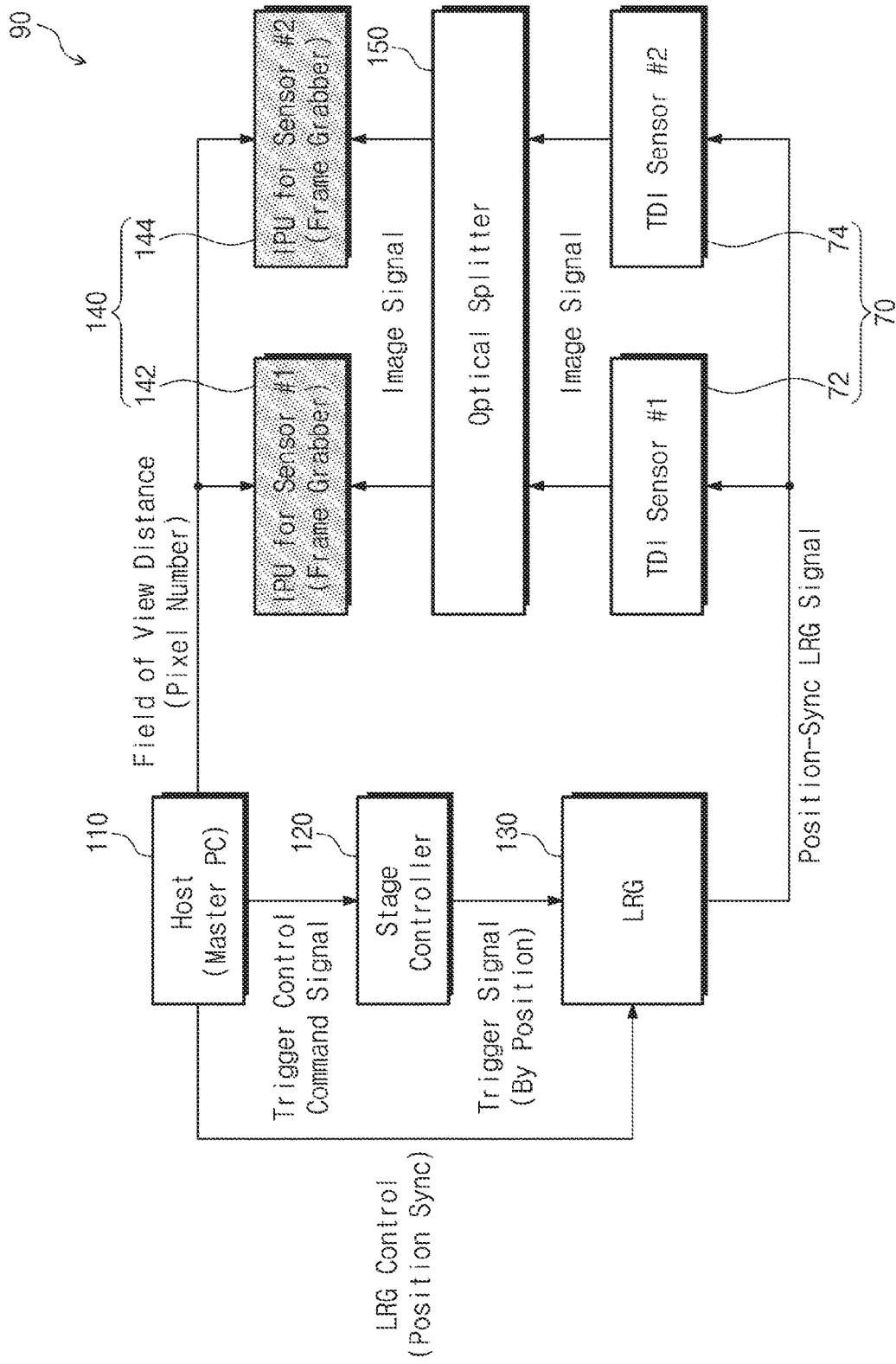
FIG. 9 is a block diagram illustrating a control module of FIG. 1.

FIG. 9 shows the control module 90 of FIG. 1.

Referring to FIG. 9, the control module 90 may include a host 110, a stage controller 120, an LRG (Line Rate Generator) 130, and IPUs (Image Processing Units) 140.

The host 110 may control the stage controller 120, the LRG 130, and the IPUs 140. For example, the host 110 may include a master personal computer including a memory (not shown) and a processor (e.g., CPU, not shown) that, when executing instructions according to software stored in the memory and/or externally received instructions through an input/output device (not shown), configures the processor of the host as a special-purpose processor for controlling one or more operations of the control module 90. The stage controller 120 may include a motor for driving the stage in response to commands from the host 110.

The stage controller 120 may control the stage 10 of FIG. 1. The stage controller 120 may output a trigger signal of the stage 10 to the LRG 130 in response to a trigger control command signal of the host 110.

The LRG 130 may determine speed and direction of the stage 10 in response to the trigger signal. The LRG 130 may output an LRG signal to the first and second sensors 72 and 74. In some example embodiments, the LRG 130 may include an application-specific integrated circuit (ASIC) or controller for generating the LRG signal based on the trigger signal. The LRG signal may be synchronized with a position of the stage 10. Based on the synchronized LRG signal and the trigger signal, the first and second sensors 72 and 74 may sequentially produce image signals of the substrate W.

The IPUs 140 may be connected through an optical splitter 150 to the first and second sensors 72 and 74. For example, the IPUs 140 may include frame grabbers. In some example embodiments, the IPUs 140 may include a first IPU 142 connected to the first sensor 72 and a second IPU 144 connected to the second sensor 74. The first and second IPUs 142 and 144 may separately and/or independently process image signals of the first and second sensors 72 and 74. The first and second IPUs 142 and 144 may be hardware processors (e.g., CPUs) and/or integrated circuits that are configured to independently process image signals of the overlapping regions 24 of the first and second sensors 72 and 74 in a manner of TDI (Time Delay and Integration) line scanning. For example, an image signal processing by the first IPU 142 may be delayed by first pixels 73 and/or second pixels 75 corresponding to a distance between the first and second sensors 72 and 74. The first and second IPUs 142 and 144 may process an image signal to obtain an image of the substrate W. The first and second IPUs 142 and 144 may align a plurality of images of the first and second sensor 72 and 74 and remove a portion of the plurality of images of the overlapping regions 24. The first and second IPUs 142 and 144 may process an entire image of the substrate W faster than a single IPU (not shown).

It will be explained below a method of manufacturing a semiconductor device using the inspection apparatus 100 configured as describe above.

Figure 10:
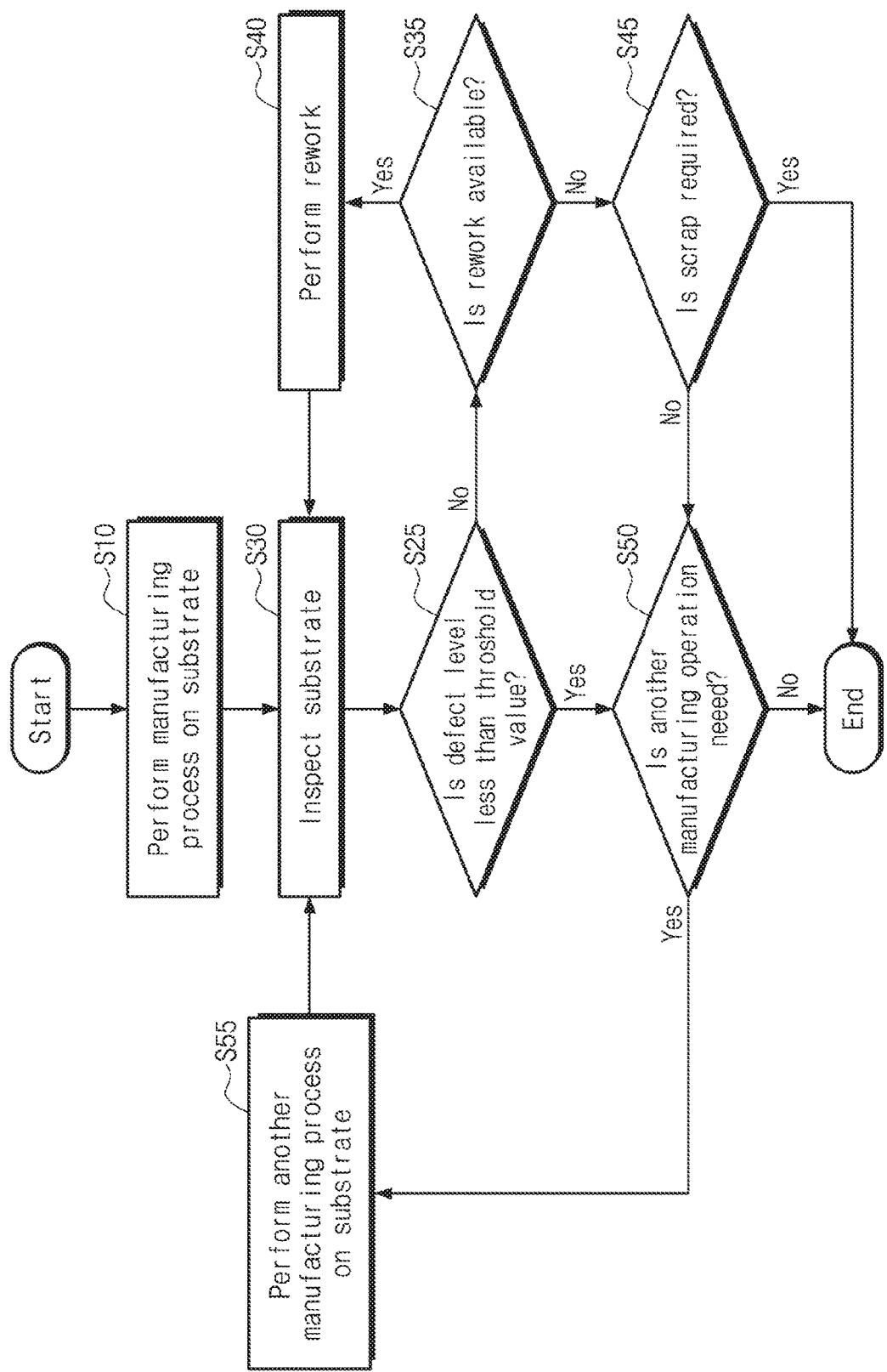
FIG. 10 is a flow chart illustrating a method of manufacturing a semiconductor device using the inspection apparatus of FIG. 1.

FIG. 10 is a flow chart illustrating a method of manufacturing a semiconductor device using the inspection apparatus 100 of FIG. 1.

Referring to FIG. 10, in some example embodiments, a manufacturing method of a semiconductor device may include processing a substrate W (S10) and inspecting the substrate W (S20).

The method in FIG. 10 may be used to form semiconductor devices 18 be formed through unit processes. For example, the unit processes may include a thin-film deposition process, a photolithography process, an etching process, a cleaning process, an ion implantation process, and/or an ashing process. Unit processing apparatus may form the semiconductor devices 18 on a top surface of the substrate W.

First, a first manufacturing process (e.g., etch, lithography, deposition, planarization, etc.) may be performed on the substrate W (S10). Subsequently, the inspection apparatus 100 may inspect the substrate W (S20). For example, the inspection apparatus 100 may optically and/or electromagnetically inspect defects of the substrate W. Defects may be detected using various methods. For example, defects may be detected based on locations on the substrate W that have a large contrast compared to adjacent locations and/or based on locations to that have patterns that do not match reference patterns.

Next, in operation (S25), the level of defects may be compared to a threshold value (e.g., upper control limit). In operation (S25), if (and/or in response to) the level of defects is greater than the threshold value, operation (S35) may be performed to determine whether a rework operation (or other operation such as a cleaned) may be performed. For example, if the first manufacturing process (S10) was a lithography patterning process, then rework may be available in operation (S35) and a rework operation (S40) may be performed.

If the first manufacturing process (S10) was a process (e.g., metal etch) where rework may not be available, a determination will be made whether the substrate W should be scrapped (S45). If the substrate W does not need to be scrapped (S45), or if (and/or response to) the defect level is less than the threshold value in operation (S25), then the method may proceed to operation (S50) to determine whether another manufacturing process is needed to form the semiconductor devices 18 (see FIG. 2). If necessary to form the semiconductor devices 18, another manufacturing process (S55) may be performed on the substrate W and then the inspection apparatus 100 may inspect the substrate W (S20) and proceed to operation (S25) to determine whether the level of defects on the substrate W is less than a threshold value. The threshold value for the defect level on the substrate W after operation S55 is performed may be the same as or different than the threshold value for the defect level on the substrate after operation S10 is performed.

Figure 11:
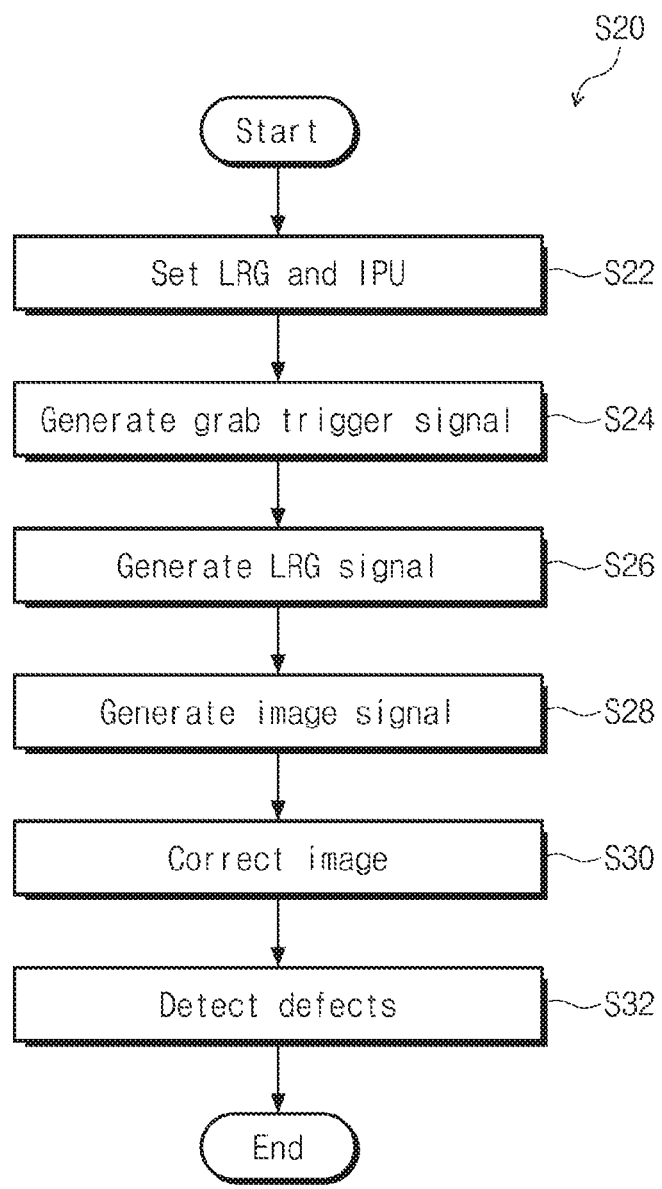
FIG. 11 is a flow chart illustrating an example of a substrate inspection operation of FIG. 10.

FIG. 11 shows an example of the substrate inspection operation S20 shown in FIG. 10.

Referring to FIGS. 9 and 11, the operation S20 of inspecting the substrate W may include setting position values of the stage 10 and the sensors 70 (S22), generating a grab trigger signal (S24), generating an LRG signal (S26), generating an image signal (S28), correcting an image (S30), and detecting defects (S32).

In the operation S22, the host 110 may set the stage controller 120, the LRG 130, and the IPUs 140 with the position values of the stage 10 and the sensors 70. For example, the host 110 may set the position values in the image plane 16 according to the pixel number of the sensors 70.

In the operation S24, the stage controller 120 may generate the grab trigger signal. The grab trigger signal may include information about a position of each of the first and second sensors 72 and 74. The stage controller 120 may output the grab trigger signal to the LRG 130.

In the operation S26, the LRG 130 may receive the generated grab trigger signal to generate the LRG signal. The LRG 130 may output the grab trigger signal and the LRG signal to the sensors 70.

In the operation S28, based on the grab trigger signal, the first and second sensors 72 and 74 may generate image signals corresponding to the top surface of the substrate W in the image plane 16. The first and second sensors 72 and 74 may output the image signals to the IPUs 140. The IPUs 140 may receive the generated image signals.

In the operation S30, the first and second IPUs 142 and 144 may acquire an image of the substrate W from the image signals, and correct a portion of the image in the overlapping region 24 of the sensors 70. The first IPU 142 may partially acquire the image based on the grab trigger signal. Before the first IPU 142 partially acquires the image, the second IPU 144 may partially acquire in advance the image of the substrate W based on the grab trigger signal. In some example embodiments, the operation S30 of correcting the image in the overlapping region 24 may be performed in a manner of TDI (Time Delay and Integration) line scanning.

In the operation S32, the host 110 may detect defects in the image. For example, the host 110 may detect defects by comparing the image with a pre-stored reference image.

According to some example embodiments of inventive concepts, an inspection apparatus may include a plurality of sensors arranged in a y-axis direction in an image plane of lenses. When a substrate moves in an x-axis direction, an image of the substrate in the image plane may be detected along the x-axis direction by the sensors. It may be possible to maximally increase quantity of reflected light detected by the sensors. Image signals of the sensors may be separately processed by a plurality of IPUs provided in a control module. The plurality of IPUs may process the image signals faster than a single IPU. As a result, the inspection apparatus may process images at high speeds.

Although some example embodiments have been described, it will be understood to those skilled in the art that various changes and modifications may be made without departing from the technical spirit and scope of inventive concepts in the following claims. It therefore will be understood that the embodiments described above are just illustrative, not for the purposes of limitation.

What is claimed is:

1. An inspection apparatus, comprising:
   a stage configured to receive a substrate;
   an objective lens on the stage, the objective lens configured to enlarge the substrate optically such that the substrate becomes an enlarged substrate;
   an ocular lens on the objective lens, the ocular lens being configured to form at its image plane an image of the enlarged substrate; and a plurality of sensors above the ocular lens and in the image plane of the ocular lens.

2. The inspection apparatus of claim 1, wherein
a shape of the image plane is a circle, and
each of the plurality of sensors have a shape corresponding to a quadrangle in the circle.

3. The inspection apparatus of claim 2, wherein a diagonal distance of the shape of each of the plurality of the sensors is greater than a radius of the circle.

4. The inspection apparatus of claim 3, wherein each of the diagonal distances of the shapes of the plurality of the sensors is inclined at a tilt angle of $3\pi/8$ relative to one side of the quadrangle.

5. The inspection apparatus of claim 2, wherein
the stage is configured to move the substrate in a first direction, and
the plurality of sensors are spaced apart from each other in a diagonal direction between the first direction and a second direction perpendicular to the first direction.

6. The inspection apparatus of claim 2, wherein
the plurality of sensors include first sensors and a second sensor,
the first sensors are on edges of the circle,
the second sensor is adjacent to a center of the circle,
a size of the second sensor is greater than a size of the first sensors, and
the center of the circle is between the first sensors.

7. The inspection apparatus of claim 6, wherein
each of the first sensors includes first pixels,
the second sensor includes second pixels,
a size of the second pixels is equal to a size of the first pixel.

8. The inspection apparatus of claim 1, further comprising:
a printed circuit board, wherein
a top surface of the printed circuit board corresponds to the image plane and is mounted with the plurality of sensors.

9. The inspection apparatus of claim 1, further comprising:
a beam splitter between the objective lens and the ocular lens; and
a light source configured to provide incident light to the beam splitter, wherein the beam splitter is configured to provide the incident light through the objective lens to the substrate and to provide the ocular lens with light reflected from the substrate.

10. The inspection apparatus of claim 9, further comprising:
a collimator between the beam splitter and the light source, wherein
the collimator is configured to collimate the incident light provided to the beam splitter.

11. A method of manufacturing a semiconductor device, the method comprising:
performing a first manufacturing process on a substrate; and
inspecting the substrate using an inspection apparatus after the performing the first manufacturing process on the substrate to detect a level of defects on the substrate, the inspection apparatus including,
a stage configured to receive the substrate,
an objective lens on the stage and configured to enlarge the substrate optically such that the substrate becomes an enlarged substrate,
an ocular lens on the objective lens and configured to form at its image plane an image of the enlarged substrate, and
a plurality of sensors above the ocular lens and in the image plane of the ocular lens; and
performing a second manufacturing process on the substrate based on the level of defects on the substrate detected during the inspecting the substrate.

12. The method of claim 11, wherein inspecting the substrate includes:
setting position values of the stage and the plurality of sensors;
generating image signals based on the position values;
acquiring an image of the substrate using the image signals and correcting the image in an overlapping region of the plurality of sensors; and
detecting the defects on the substrate in the image of the substrate.

13. The method of claim 12, wherein the correcting the image includes performing a Time Delay and Integration (TDI) line scanning process.

14. The method of claim 12, further comprising:
generating a grab trigger signal using the inspection apparatus; and
generating an LRG (Line Rate Generator) signal using the inspection apparatus.

15. The method of claim 14, wherein
the inspection apparatus further includes a control module,
the control module includes a host, stage controller, Line Rate Generator (LRG), and a plurality of Image Processing Units (IPUs),
the stage controller is connected to the host,
the stage controller is configured to generate the grab trigger signal and to control the stage,
the LRG is connected between the stage controller and the sensors,
the LRG is configured to generate the LRG signal,
the plurality of IPUs are connected between the host and the sensors, and
the plurality of the IPUs are configured to process the image signals.

16. An inspection apparatus, comprising:
a stage configured to receive a substrate and to move the substrate in a first direction;
an optical system configured to form an enlarged image of the substrate at an image plane; and
a plurality of sensors arranged in the image plane, the plurality of sensors being configured to sense part of the enlarged image of the substrate, the plurality of sensors including a first sensor and a second sensor, the first sensor including an overlapping region that is spaced apart from an overlapping region of the second sensor in the first direction.

17. The inspection apparatus of claim 16, wherein
the optical system includes an objective lens over the stage and an ocular lens over the objective lens,
a shape of the image plane is a circle,
each of the plurality of sensors have a shape corresponding to a quadrangle in the image plane, and
a diagonal distance of the shape of each of the plurality of the sensors is greater than a radius of the image plane.

18. The inspection apparatus of claim 16, further comprising:
a control module configured to scan the substrate in a second direction using the optical system and the plurality of sensors, wherein the second direction is opposite the first direction,
the control module includes a host and a plurality of image processing units (IPUs)
the plurality of the IPUs are configured to separately process image signals generated using the plurality of the sensors.

19. The inspection apparatus of claim 16, wherein a size of the first sensor is different than a size of the second sensor.

20. The inspection apparatus of claim 16, wherein a size of the first sensor is equal to a size of the second sensor.

* * * * *